US008445513B2

(12) United States Patent     (10) Patent No.:   US 8,445,513 B2
Besana et al.     (45) Date of Patent:   May 21, 2013

(54) α-AMINOAMIDE DERIVATIVES USEFUL IN THE TREATMENT OF RESTLESS LEGS SYNDROME

(75) Inventors: Claudia Besana, Bresso (IT); Elena Barbanti, Cologno Monzese (IT); Emanuela Izzo, Gerenzano (IT); Florian Thaler, Bresso (IT); Ruggero Fariello, Bresso (IT); Patricia Salvati, Bresso (IT); Luca Benatti, Bresso (IT)

(73) Assignee: Newron Pharmaceuticals S.p.A., Bresso (IT)

( * ) Notice: Subject to any disclaimer, the term of this patent is extended or adjusted under 35 U.S.C. 154(b) by 163 days.

(21) Appl. No.: 11/578,988

(22) PCT Filed: Apr. 19, 2005

(86) PCT No.: PCT/EP2005/004166
§ 371 (c)(1),
(2), (4) Date: Dec. 19, 2006

(87) PCT Pub. No.: WO2005/102300
PCT Pub. Date: Nov. 3, 2005

(65) Prior Publication Data
US 2007/0203182 A1    Aug. 30, 2007

(30) Foreign Application Priority Data

Apr. 22, 2004   (EP) ....................................  04009532

(51) Int. Cl.
*A61K 31/445*      (2006.01)
*A61K 31/40*      (2006.01)
*A61K 31/277*      (2006.01)
*A61K 31/165*      (2006.01)
*A61K 31/137*      (2006.01)

(52) U.S. Cl.
USPC ........... 514/317; 514/521; 514/620; 514/621; 514/649; 514/408

(58) Field of Classification Search
None
See application file for complete search history.

(56) References Cited

U.S. PATENT DOCUMENTS

| | | | |
|---|---|---|---|
| 4,049,663 A | | 9/1977 | Harper et al. |
| 4,513,009 A | | 4/1985 | Roques et al. |
| 4,935,429 A | | 6/1990 | Dackis et al. |
| 4,970,200 A | | 11/1990 | Birkmayer et al. |
| 5,236,957 A | * | 8/1993 | Dostert et al. ............... 514/620 |
| 5,391,577 A | | 2/1995 | Dostert et al. |
| 5,502,079 A | | 3/1996 | Dostert et al. |
| 5,945,454 A | * | 8/1999 | Pevarello et al. ............ 514/620 |
| 6,217,905 B1 | | 4/2001 | Edgren et al. |
| 6,258,827 B1 | | 7/2001 | Chenard et al. |
| 6,306,903 B1 | | 10/2001 | Pevarello et al. |
| 6,500,867 B1 | | 12/2002 | Virkki et al. |
| 2002/0019421 A1 | | 2/2002 | Biberman |
| 2007/0203182 A1 | | 8/2007 | Besana et al. |

FOREIGN PATENT DOCUMENTS

| | | |
|---|---|---|
| EP | 0 400 495 | 12/1990 |
| EP | 0 520 325 | 12/1992 |
| GB | 1140748 | 1/1969 |
| WO | WO 90/14334 A1 | 11/1990 |
| WO | WO 94/22808 A1 | 10/1994 |
| WO | WO 97/05102 A1 | 2/1997 |
| WO | WO 97/05111 A1 | 2/1997 |
| WO | WO 99/35123 A1 | 7/1999 |
| WO | WO 99/35125 A1 | 7/1999 |
| WO | 01/34172 A2 | 5/2001 |
| WO | 01/41763 A1 | 6/2001 |
| WO | 03/099763 A1 | 12/2003 |
| WO | 2004/007429 A1 | 1/2004 |
| WO | WO 2004/089353 A2 | 10/2004 |
| WO | 2005/040138 A1 | 5/2005 |
| WO | WO 2005/102300 A1 | 11/2005 |

OTHER PUBLICATIONS

Rigsman et al., "Secondary periodic limb movement disorder and restless legs syndrome." Sleep Medicine Reviews 1999:3(2);147-158.*
Kishore et al., "Drug management of Parkinson's disease." Canadian Family Physician 1996:42;946-952.*
Hening et al., "The Treatment of Restless Legs Syndrome and Periodic Limb Movement Disorder." Sleep 1999:22(7);970-999.*
Drake, M. E., "Restless Legs with Antiepileptic Drug Therapy," *Clinical Neurology and Neurosurgery* 90, No. 2:151-154, Abstract Only (1988).
Raj, P. Prithvi, "Chapter 19: Pain Syndromes in Selected Neurological Disorders by Spillane, W.," *Practical Management of Pain*, 3rd Edition, Elsevier Health Services (2000).
Singh et al., "Restless Legs Syndrome," *J. Indian Academy of Clin. Med.* 9(3):188-192 (2008).
Trenkwalder et al. "Treatment of restless legs syndrome: an evidence-based review and implications for clinical practice," *Movement Disorders: Official Journal of the Movement Disorder Society*, 23, No. 16:2267-2302 (Dec. 15, 2008).
"Treatment of Periodic Limb Movements in Sleep With Selegiline HC1", Grewal et al., Movement Disorders 2002 United States, vol. 17, No. 2, 2002, pp. 398-401, XP008035546.
"A Preliminary Placebo-Controlled Trial of Selegiline Hydrochloride for Smoking Cessation", George et al., Biological Psychiatry, vol. 53, No. 2, Jan. 15, 2003, pp. 136-143, XP008035557.
"Transdermal Selegiline and Intravenous Cocaine: Safety and Interactions", Houtsmuller et al., Psychopharmacology, vol. 172, No. 1, Feb. 2004, pp. 31-40, XP002297167.
"Pressor Response to Intravenous Tyramine in Healthy Subjects After Safinamide, a Noel Neuroprotectant With Selective, Reversible Monoamine Oxidase B Inhibition," Carlo Cattaneo et al., Clinical Neuropharmacology, pp. 213-217, 2003 XP008035545.

(Continued)

*Primary Examiner* — Walter Webb
(74) *Attorney, Agent, or Firm* — Lucas & Mercanti, LLP

(57) ABSTRACT

The invention relates to the use of certain alpha-aminoamide derivatives in the treatment of RLS and addictive disorders. The compounds of this invention are able to reduce or even stop the symptoms of RLS and addictive disorders substantially without side effects.

14 Claims, 6 Drawing Sheets

OTHER PUBLICATIONS

"Restless Legs Syndrome and Its Treatment by Dopamine Agonists," K. Stiasny et al., Parkinsonism and Related Disorders 2000 United Kingdom, vol. 7, No. 1, 2000, pp. 21-25, XP000992182.

Effects of co-administration of anticonvulscant and putative anticonvulsive agents and sub-/suprathreshold doses of L-Dopa upon motor behaviour of MPTP-treated mice, A. Fredriksson et al., Journal of Neural Transmission, vol. 106, No. 9-10, 1999, pp. 889-909.

"Symbiotic Approach to Drug Design," B.J.R. Nicolaus, Decision Making in Drug Research, 1983, pp. 173-186, XP002197412.

"Medicinal Compositions Containing Adenosine A2A Receptor Antagonists and Dopamine Agonists," Hiroshi Kase et al., STN Database, XP002338293, Date: Jul. 23, 2004.

Anonymous: "Newron Releases Positive Preliminary Phase II Data for Salfinamide in Parkinson's Disease" Press Release of Mar. 1, 2003, Retrieved from the Internet: <URL: http://www.newron.com/uploads/SafinamidePhaseIIdataFinal090103.pdf on Feb. 18, 2009.

Anonymous: "Newron Pharmaceuticals S.p.A. Announces Data of Phase I Clinical Trials of Its Anti-epileptic and Anti-Parkinson Compound NW-1015," Press Release of Mar. 14, 2000, Retrieved from the Internet: <URL: http://www.newr on.com/uploads/AnnouncesdataofphaseIclinicaltrials.pdf; on Feb. 18, 2009.

Archer, T. et al., 2002, "Restorative Effects of Glumate Antagonists in Experimental Parkinsonism," Amino Acids, 23:71-85.

Bailey et al., 1975, "The Mechanism of Action of Amantadine in Parkinsonism: A Review," Arch. Int. Pharmacodyn. Ther., 216: 246-262.

Benedetti, S. et al., 1994, "The Anticonvulsant FCE 26743 is a Delective and Short-Acting MAO-B Inhibitor Devoid of Inducing Properties Towards Cytochrone P450-dependent Testosterone Hydroxylation in Mice and Rats," J. Pharm. Pharmacol. 46:814-819.

Berlin, I. et al., 2002, "Lazabemide, a Selective, Reversible Monoamine Oxidase B Inhibitor, as an Aid to Smoking Cessation," Addiction 97:1347-1354.

Blanduni F. et al., 1996, "Glutamate and Parkinson's disease," Mol Neurobiol., 12, 73-94.

Caine S. B. et al., 2000, "Effects of dopamine D1-like and D2-like agonists on cocaine self-administration in rhesus monkeys: rapid assessment of cocaine dose-effectfunctions," Psychopharmacology 148:41-51.

Caine, S. B. et al., 1993, "Intravenous drug self-administration techniques in animals," Behavioral Neuroscience: A Practical Approach, ed. by A. Sahgal, 117-143.

Calzetti, S. et al., 2009, "Absence of co-morbidity of Parkinson disease and restless legs syndrome: a case-control study in patients attending a movement disorders clinic," Neurological Sciences 30(2).

Chase, T, 1998, "The Significance of Continuous Dopaminergic Stimulation in the Treatment of Parkinson's Disease," Drugs, 55 (Suppl. 1): 1-9.

Chazot, P., 2001, "Salfinamide, Newron Pharmaceuticals," Current Opinion in Invest. Drugs, 2(6): 809-813.

Clarke, C. E., 2002, "Medical Management of Parksinon's Disease," J Neurol Neurosurg Psychiatry 72 (Suppl. 1) i22-i27.

Communication for European Patent Application 04 726 590.5-2123 mailed Dec. 5, 2006.

Colpaert, F. C., 1986, "Drug Discrimination: Behavioral, Pharmacological and Molecular Mechanisms of Discriminative Drug Effects," Behavioral Analysis of Drug Dependence, Goldberg and Stolerman, IP eds, 161-193.

Cotter, P. et al., 2006, "Restless leg syndrome: is it a real problem?," Ther. and Clin. Risk Management, 2, 465-475.

Facca, A. et al., 2003, "Differential Diagnosis of Parkinsonism," Adv Neurol, 91:383-396.

Fariello, R. G. et al., 1998, "Preclinical Ecaluation of PNU-151774E as a Novel Anti-convulsant," J. Pharmacol. Exp. Ther. 285: 397-403.

Fischman, M. W., 1988, "Behavioral Pharmacology of Cocaine," J. Clin Psychiatry, 49 Suppl:7-10.

Garcia-Borreguero D. et al., 2003, "Restless legs syndrome and PD: A review of the evidence for a possible association," Neurology, 61, 549-855.

Gomez-Esteban, J. C. et al., 2007, "Restless legs syndrome in Parkinson's disease," Mov. Disord 22, 1912-1916.

Heikkila, R. et al., 1984, "Protection Against the Dopaminergic Neurotoxicity of 1-Methyl-4-Pheny1-1,2,5,6-Tetrahydropyridine by Monoamine Oxidase Inhibitors," Nature 311: 467-469.

International Preliminary Examination Report and Written Opinion of PCT/IB2004/001408.

International Preliminary Examination Report of PCT/EP2005/004166.

International Search Report of PCT/IB2004/001408.

International Search Report of PCT/EP2005/004166.

Jellinger, K. A., 1999, "Post mortem studies in Parkinson's disease—is it possible to detect brain areas for specific symptoms?", J. Neural Transm., Suppl. 56,1-29.

Johnson, B. et al, 2003, "Oral Topiramate for Treatment of Alcohol Dependence: A Randomised Controlled Trial," The Lancet 361:1677-1685.

Katz J. L. et al., 1999, "Behavioral Effects of Cocaine: Interactions with D1 Dopaminergic Antagonists and Agonists in Mice and Squirrel Monkeys," J Pharmacol Exp Ther. 291(1):265-79.

Koob, G.F. et al., 1998, "Neuroscience of Addiction," Neuron 21, 467-476.

Krishnan, P. R. et al., 2003, "Restless legs syndrome in Parkinson's Disease: a case-controlled study," Mov. Disord., 18, 181-185.

Lamas X. et al., 1995, "Relationship Between the Discriminative Stimulus Effects and Plasma Concentrations of Intramuscular Cocaine in Rhesus Monkeys," Psychopharmacology 121:331-338.

Lees, A. J., 2002, "Drugs for Parkinson's Disease," J Neurol Neurosurg Psychiatry 73:607-610.

Mai, R. et al., 1999, "PNU-141774E, A Combined MAO-B and Glutamate Release Inhibitor, is Effective in Animal Models of Parkinson's Disease," Society for Neuroscience, vol. 25, 1599.

Mann et al., 1971, "Amantadine for Parkinson's Disease," Neurology, 21: 958-962.

Marjama-Lyons, J. et al., 2001, "Parkinson's Disease: Update in Diagnosis and Symptom Management," Geriatrics Aug.; 56(8):24-25, 29-30, and 33-35.

Marsden et al; 1997, "Success and Problems of Long-Term Levodopa Therapy in Parkinson's Disease," Lancet Feb. 12, 1997: 345-349.

Meldrum, B., 1994, "The Role of Glutamate in Epilepsy and Other CNS Disorders," Neurology, 44 (Supp. 8) 814-823.

Mello, N. K. et al., 1996, "Preclinical Evaluation of Pharmacotherapies for Treatment of Cocaine and Opioid Abuse Using Drug Self Administration Procedures," Neuropsychopharmacology 14:375-424.

Minutes of Oral Hearing (Nov. 19, 2007) for EP 04 726 590.5-2123.

Mytilineou, C. et al., 1997, "L-Deprenyl Protects Mesencephalic Dopamine Neurons from Glutamate Receptor-Mediated Toxicity In Vitro," J Neurochem. 68: 33-39.

Negus S.S. et al., 1996, "Acute and Chronic Effects of Flupenthixol on the Discriminative Stimulus and Reinforcing Effects of Cocaine in Rhesus Monkeys," J Pharmacal Exp Ther 278:879-890.

Negus S.S. et al., 1995, "Role of Delta Opioid Receptors in the Reinforcing and Discriminative Stimulus Effects of Cocaine in Rhesus Monkeys," J Pharmacol Exp Ther 273:1245-1256.

Negus S.S. et al., 1999, "Effects of the Long-Acting Monoamine Reuptake Inhibitor Indatraline on Cocaine Self-Administration in Rhesus Monkeys.," J Pharmacol Exp Ther 291:60-69.

Negus, S. S. et al., 1997, "Effects of Kappa Opioids on Cocaine Self-Administration by Rhesus Monkeys," J Pharmacal Exp Ther 282: 44-55.

Nomura et al., 2006, "Prevalence and clinical characteristics of restless legs syndrome in Japanese patients with Parkinson's Disease," Mov. Disord., 21, 380-384.

Office Action for U.S. Appl. No. 10/559,982 mailed Oct. 15, 2008.

Office Action for U.S. Appl. No. 10/559,982 mailed Dec. 24, 2008.

Ondo W. et al., 2002, "Exploring the relationship between Parkinson Disease and restless legs syndrome," Mch. Neurol., 58, 421-424.

Parkes , J. D, et al., 1971, "Treatment of Parkinson's Disease with Amantadine and Levodopa," Lancet, 21: 1083-1086.

Pevarello P. et al., 1998, Synthesis and Anticonvulsant Activity of a New Class of 2-[(Arylalkyl)amino]alkanamide Derivatives, J. Med. Chemistry, 41: 579-590.

Phillips, B. et al., 2000, "Epidemiology of Restless Legs Syndrome in Adults," Archives of Internal Medicine 160 (14) 2137-2141.

Poewe, W., 1993, "Clinical Features, Diagnosis, and Imaging of Parkinsonian Syndromes," *Curr Opin Neurol Neurosurg* Jun.; 6(3):333-338.

Povedano et al. 2007, "Cognitive Function Impairment in Patients with Neuropathic Pain Under Standard Conditions of Care," *J. Pain Symptom Management*, 33(1), 78-89.

Remington's Pharmaceutical Sciences 15th Edition, pp. 1035-1038 and 1570-1580, (1975).

Response to Exam Report for European Patent Application 05 736 365.7-1216 mailed Jul. 10, 2007.

Robinson T.E. et al., 1993, "The Neural Basis of Drug Craving: An Incentive-Sensitization Theory of Addiction," *Brain Res Rev* 18, 247-91.

Ruottinen, H.M. et al., 2000, "An FDOPA PET Study in Patients with Periodic Limb Movement Disorder and Restless Leg Syndrome," *Neurology* 54: 502-504.

Ryan, M. et al., 2007, "Restless Leg Syndrome," *Journal of Pharmacy Practice*, 20: 430-448.

Salvati, P. et al., 1999, "Biochemical and Electrophysiological Studies on the Mechanism of Action of PNU-151774E, A Novel Antiepileptic Compound," *Pharmacol. Exp. Ther.* 288:1151-1159.

Satija P. et al., 2008, "Restless legs syndrome: pathophysiology, diagnosis and treatment," *CNS Drugs*, 22, 497518.

Schiffer. W. et al., 2003, "Selegiline Potentiates Cocaine-Induced Increases in Rodent Nucleus Accumbens Dopamaine," *Synapse* 48:35-8.

Siderowf, A., 2001, "Parkinson's Disease: Clinical Features, Epidemiology, and Genetics," *Movement Disorders* Aug.;19(3):565-578.

Sofuoglu, M. et al., 2005, "Novel approaches to the treatment of cocaine addiction" *CNS Drugs*, 19,(1)13-25.

Stocchi, F. et al., 2006, Symptom Relief in Parkinson Disease by Safinamide: Biochemical and Clinical Evidence of Efficacy beyond MAO-B Inhibition; *Neurology* 67(7)Suppl2:S24-S29.

Stocchi F. et al., 2004, "Improvement of Motor Function in Early Parkinson Disease by Safinamide," *Neurology* 63(4):746-748.

Sulkava, R., 2003, "Differential Diagnosis between Early Parkinson's Disease and Dementia with Lewy Bodies," *Adv Neurol*, 91:411-413.

Trenkwalder C. et al., 2005 "The restless legs syndrome," *Lancet Neurol.*, 4,465-475.

Turjanski, N. 1999, "Striatal Dopaminergic Function in Restless Legs Syndrome," *Neurology* 52, 932-937.

Vilarino-Guell C. et al., 2008, "Susceptibility genes for RLS are not associated with PD," *Neurology*, 71, 222-223.

Walters, A. S., 1995, "Toward a Better Definition of the Restless Legs Syndrome," *Movement Disorders* 10 (5) 634-642.

Woolverton, W. L., 1996, "Intravenous Self-Administration of Cocaine Under Concurrent VI Schedules of Reinforcement," *Psychopharmacology* 127: 195-203.

Written Opinion of PCT/EP2005/004166 date stamped Aug. 4, 2005.

Youdim, B. H. et al., 1991, "New Directions in Monoamine Oxidase A and B Selective Inhibitors and Substrates," *Biochem Pharmacol.* 41(2): 155-162.

* cited by examiner

Figure 1. Clinical Global Impression. Part I. Mean scores (and SD).
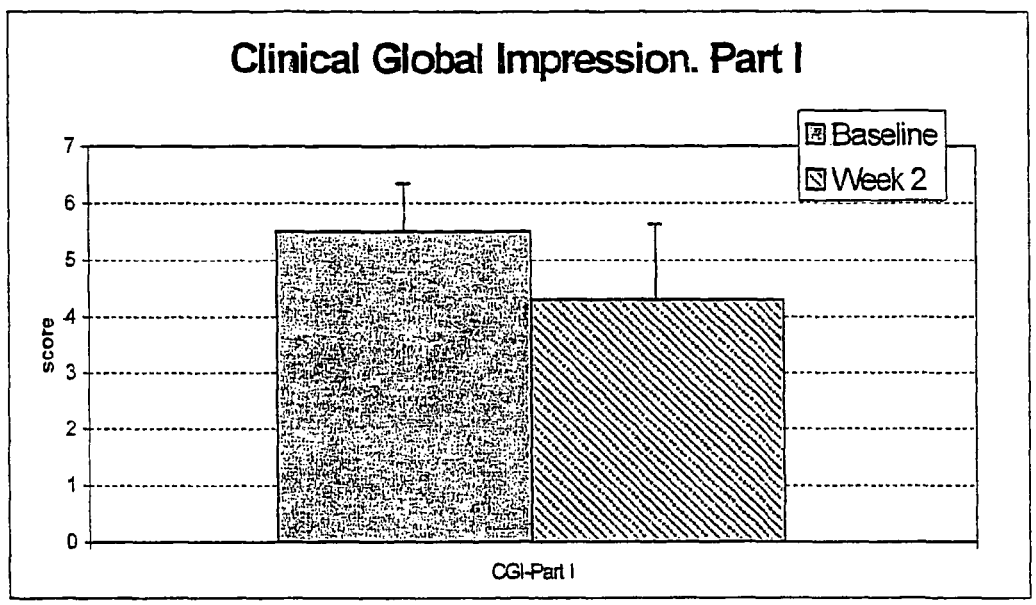

Figure 2. RLS-QoLQ. Mean values (and SD) of Total score
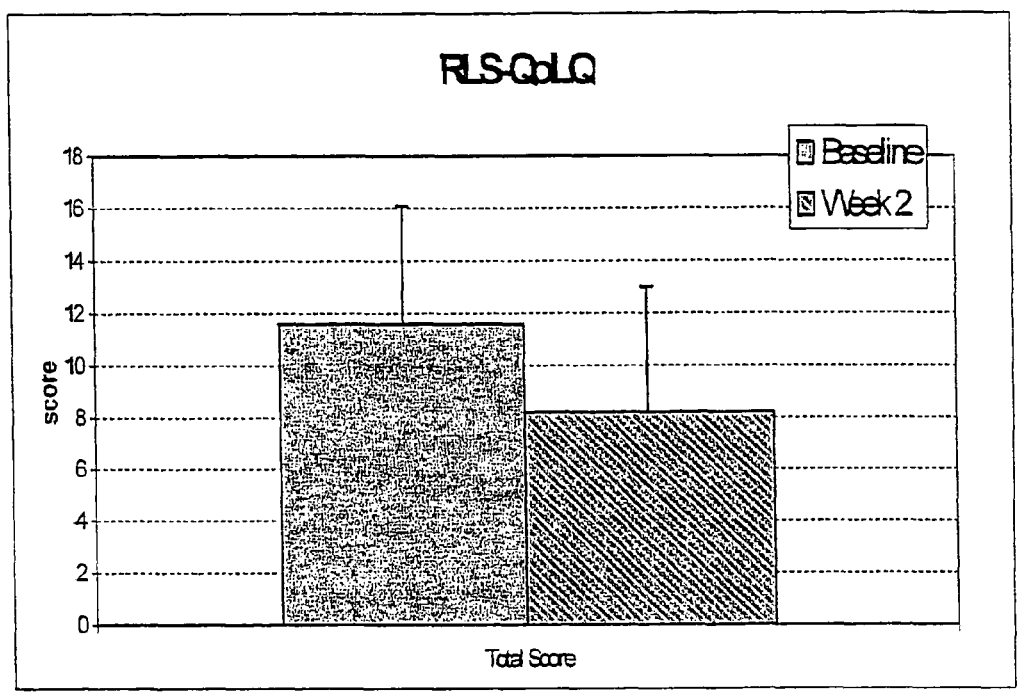

Figure 3. WPAI-RLS. Mean scores (and SD) of Item 6.
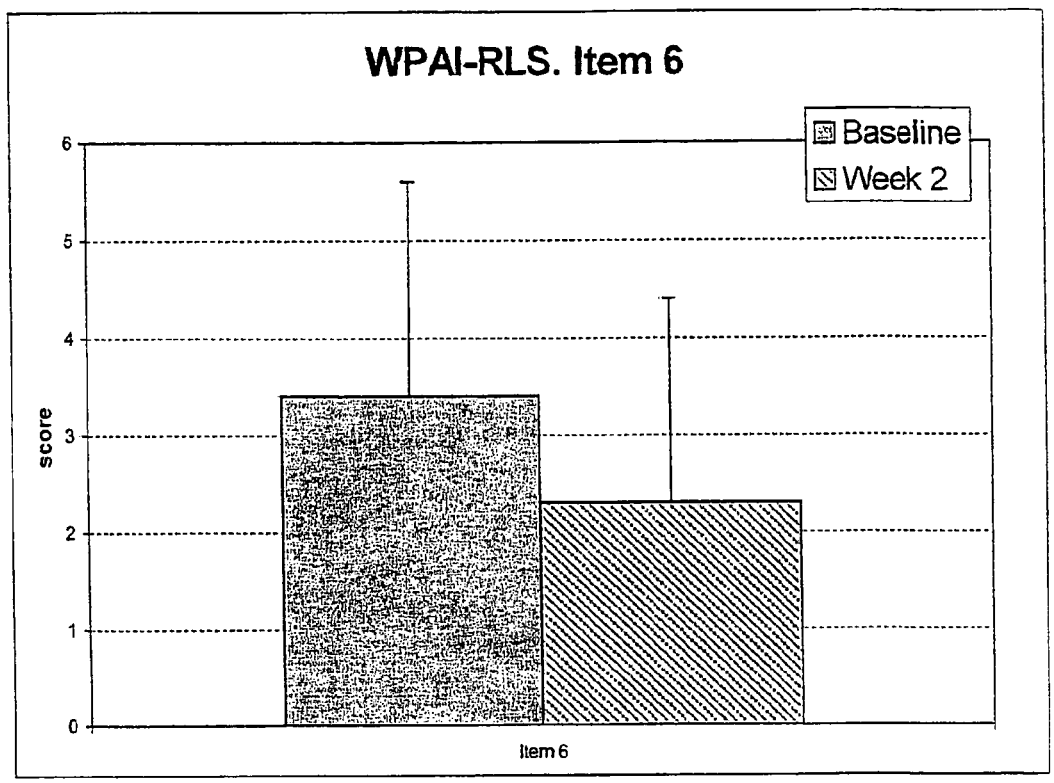

Figure 4. Polysomnography. PLM (Wake+Sleep) Index. Mean values
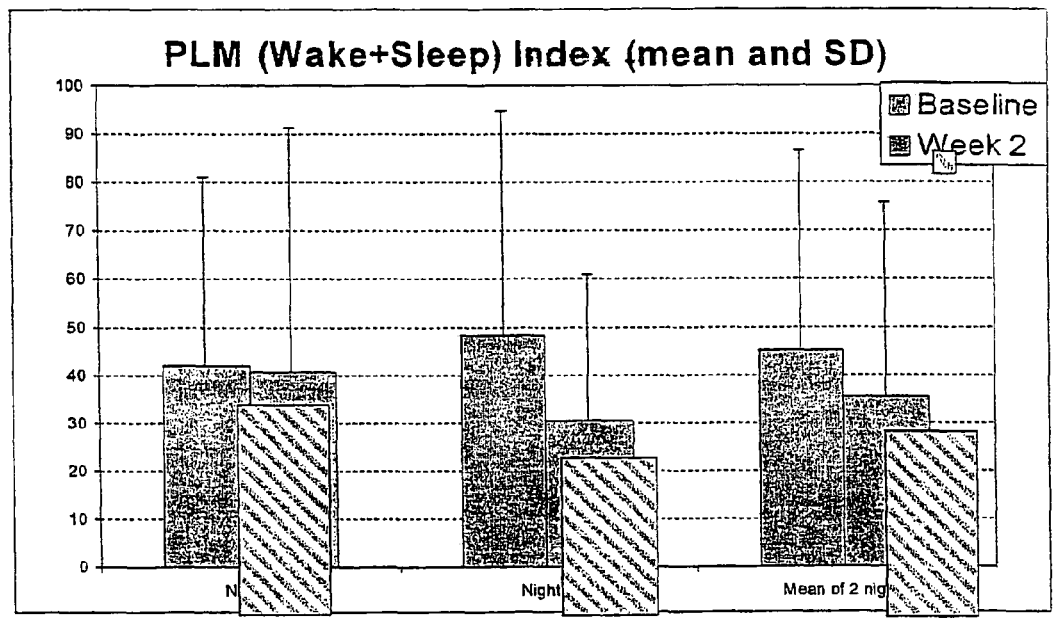

Figure 5. Polysomnography. PLM-Sleep Index. Mean values (and SD)
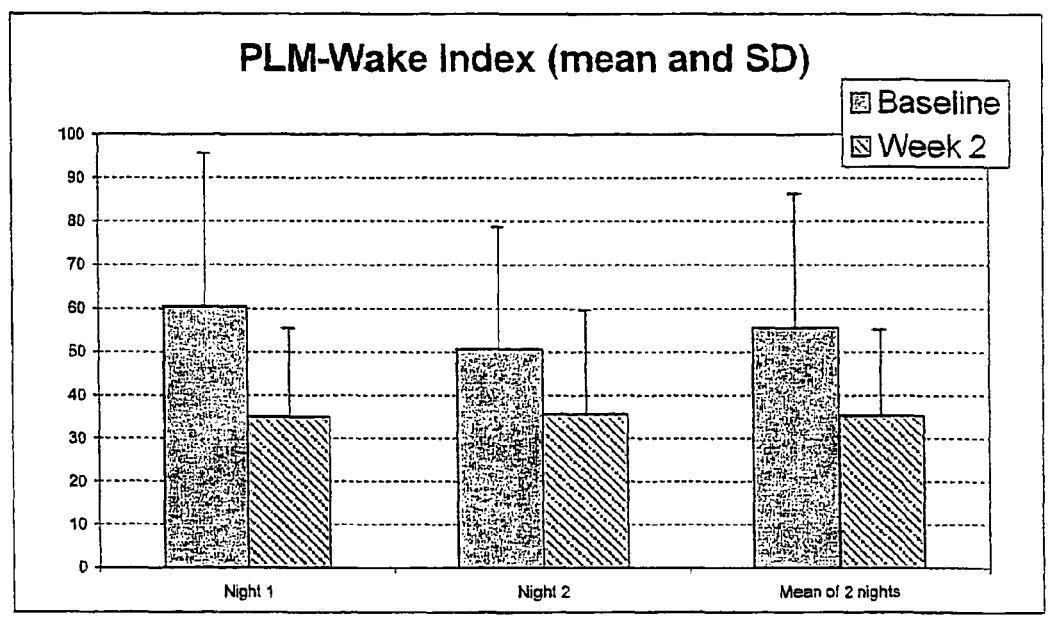

Figure 6. Polysomnography. PLM Wake Index. Mean values (and SD)
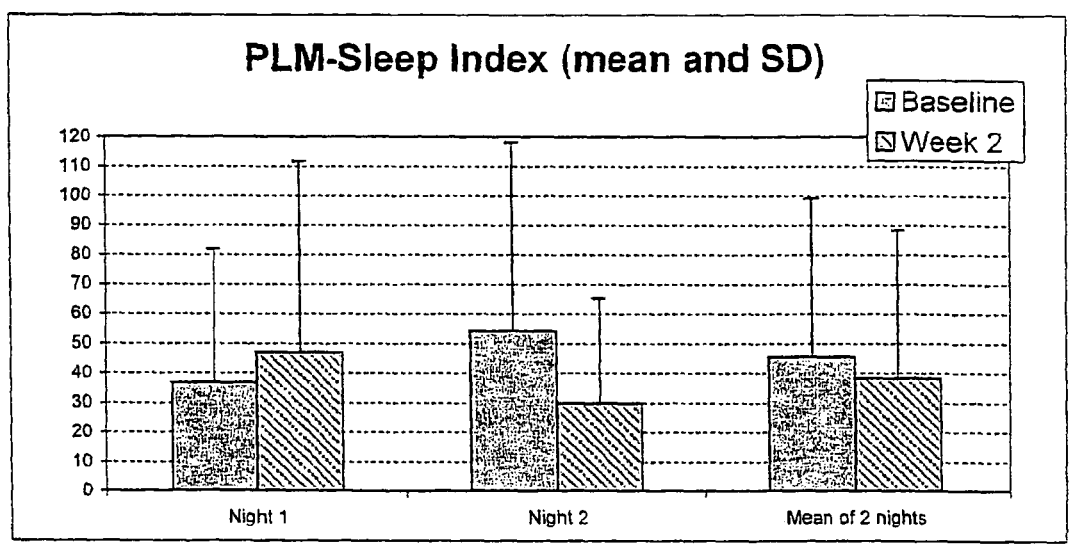

α-AMINOAMIDE DERIVATIVES USEFUL IN THE TREATMENT OF RESTLESS LEGS SYNDROME

The invention relates to α-aminoamide derivatives, a chemical class of monoamine oxidase B (MAOB) inhibitors, sodium channel blockers, dopamine reuptake inhibitors and glutamate levels modulators for use in the treatment of Restless Legs Syndrome (RLS) and addictive disorders.

BACKGROUND OF THE INVENTION

Restless Legs Syndrome (RLS) is a well defined, recognised clinical entity characterised by unpleasant creeping, burning or pulling sensations deep in the legs, between the knees and the ankles and less frequently in the arms. The symptoms are present when the limbs are at rest, particularly in the evening and at night, and are generally relieved by movement. The consequence is the appearance of sleep disturbances, prolonged sleep latency, decreased total sleep time with reduced or absent slow wave sleep and decreased sleep efficiency.

Epidemiological studies have found RLS to be common with lifetime prevalence figures in adults ranging from 9% to 15% of the general population (Phillips B *Epidemiology of restless legs syndrome in adults* Archives of Internal Medicine 160 (14) 2137-2141 2000). The international RLS Study Group Criteria (1995) defines RLS patients as presenting the following symptoms (Walters A S *Toward a better definition of the Restless Legs Syndrome* Movement Disorders 10 (5) 634-642 1995):
1. A desire to move the limbs associated with paresthesias or dysesthesias.
2. Motor restlessness (during wakefulness patients move the limbs in attempt to relieve the discomfort).
3. Symptoms worse or exclusively present at rest with at least partial and temporary relief by activity.
4. Symptoms worsen in the evening or at night.

Other common features are sleep disturbances, periodic limb movements in sleep (PLMS) and similar involuntary movement while awake (Walters A S *Toward a better definition of the Restless Legs Syndrome* Movement Disorders 10 (5) 634-642 1995).

The number of PLM and related parameters are considered to be a marker for the severity of RLS since PLM are frequently associated with nocturnal arousals or awakenings.

Because of problems during sleep and wakefulness, people with RLS may have difficulties with their job, social life and recreational activities.

The pathogenesis of RLS remains unknown, but current evidence favours a disinhibition of normal central nervous system pacemakers, probably governed by multiple influences. Positron emission tomographic (PET) studies in RLS have supported the role of the dopaminergic system in the pathogenesis of the disorder. Turjanski et al disclose that both caudate and putamen $^{18}$F-dopa uptake were mildly reduced in RLS patients compared with control subjects, and this reached significance (p=0.04) in the putamen. The same study demonstrated a significant reduction in D2 dopamine receptor binding in the putamen in these patients (Turjanski N Neurology 52 932-937 1999). Similarly, Ruottinen et al. studied a group of drug-naïve RLS patients and demonstrated an 11% decrease in $^{18}$F-dopa uptake in the putamen and 12% in the caudate nucleus (Ruottinen H M Neurology 54 502-504 2000). These data are suggestive of a mild striatal presynaptic dopaminergic dysfunction.

No agents are currently indicated for the treatment of RLS in the U.S., although Restex®, a preparation of L-dopa has recently been launched in Germany. The other products used to treat RLS symptoms include opiates, benzodiazepines and some anticonvulsants. Dopamine agonists, such as cabergoline, pramipexole and ropinirole, have been also proposed for RLS treatment. All these treatments have disadvantages such as side effects, interactions, short duration of action and abuse potential. The available evidence suggests that a deficit of dopaminergic system plays an important role in RLS. Since MAOB inhibitors affect the metabolism of dopamine leading to a prolongation of the time course of dopamine on its receptor, we propose the use of α-amino derivatives in the treatment of RLS. Other disorders, where a deficit in the dopaminergic system plays an important role, are the addictive disorders that can be defined as pathological behaviour characterized by compulsive drug seeking and intake. Continued drug use is believed to cause protracted functional changes in the neural circuits involved in motivation that can lead to dependence, drug craving and relapse.

Typically different drugs of abuse (amphetamine, cocaine, heroine, nicotine, alcohol) even with different primary molecular target have the common action of increasing dopamine transmission in the mesolimbic system. Different approaches have been used in the treatment of addiction disorders and most of them aim to modulate the dopaminergic system.

MAOB inhibitors affect the metabolism of dopamine in human and primates leading to a prolongation of the time course of dopamine on its receptors. The use of MAOB inhibitor has been shown to be beneficial in the treatment of pathologies where a dopaminergic deficit is present like in PD.

New evidences support the hypothesis that MAOB inhibitors can be beneficial in the treatment of addictive disorders. Studies performed in rats and in human have shown that selegiline (a specific MAOB inhibitor) has a moderate anti-reinforcing effect during cocaine detoxification and may improve dopamine deficits during withdrawal which are thought to contribute to relapse events (Schiffer et al, 2003 Synapse 48:35-8).

Recently it has been observed that smokers have a reduced MAOB activity in platelet and brain. It has been hypothesized that reduced MAOB activity in the brain is involved in increasing the addictive properties of nicotine. In a multi-center phase II study lazabemide, another MAOB inhibitor (200 mg/day), seems to increase the percentage of smoking cessation (from 17 to 30%) (Berlin et al, 2002 Addiction 97:1347-1354).

Moreover it has been shown that also Na channel blockers can be effective in the treatment of addictive disorders. Indeed a recent clinical study has shown that topiramate (a Na channel blocker) is efficacious in the treatment of alcohol dependence (Johnson et al, 2003, The Lancet 361: 1677-1685).

Current treatments of addictive disorders include antidepressants drugs, opiate receptor agonists like methadone, opiate receptor antagonists and partial agonists like naltrexone and buprenorphine, benzodiazepines and disulfiram for alcohol detoxification. Disadvantages of these treatments include several side effects and still an unsatisfactory therapeutic efficacy.

Since there are evidences that compounds with MAOB inhibition activity and compounds with Na channel blockers activity can be effective in the treatment of addictive disorders we propose the use of α-amino derivatives, a chemical class of monoamine oxidase B (MAOB) inhibitors and sodium channel blockers of this invention in the treatment of addictive disorders.

WO90/14334, WO94/22808, WO97/05102, WO 97/0511 and WO 99/35215, the texts of which are incorporated by reference herein, disclose substituted benzylaminopropanamide compounds active on the central nervous system and useful as anti-epileptic, anti-Parkinson, neuroprotective, antidepressant, and antispastic hypnotic agents (see also Pevarello P. et al. (1998), *J. Med. Chemistry*, 41: 579-590). WO99/35125 and WO99/35123 disclose substituted benzylaminopropanamide compounds active on the central nervous system and useful as analgesic agents.

BRIEF DESCRIPTION OF THE DRAWINGS

FIG. 1 shows Clinical Global Impression of patients treated with (S)-(+)-2-[4-(3-Fluorobenzyloxy)-benzylamino]-propanamide for two weeks.

FIG. 2 shows Restless Legs Syndrome Quality of Life of patients treated with (S)-(+)-2-[4-(3-Fluorobenzyloxy)-benzylamino]-propanamide for two weeks.

FIG. 3 shows Work Productivity and Activity Impairment Questionnaire results of patients treated with (S)-(+)-2-[4-(3-Fluorobenzyloxy)-benzylamino]-propanamide for two weeks.

FIG. 4, shows Polysomnographic Registration (Wake + Sleep) Index of patients treated with (S)-(+)-2-[4-(3-Fluorobenzyloxy)-benzylamino]-propanamide for two weeks.

FIG. 5 shows Polysomnographic Registration Sleep Index of patients treated with (S)-(+)-2-[4-(3-Fluorobenzyloxy)-benzylamino]-propanamide for two weeks.

FIG. 6 shows Polysomnographic Registration Wake Index of patients treated with (S)-(+)-2-[4-(3-Fluorobenzyloxy)-benzylamino]-propanamide for two weeks.

DESCRIPTION OF THE INVENTION

The present invention provides rapid and highly effective methods for treating RLS and addictive disorders by utilizing, in vivo, certain α-aminoamide compounds in a therapy which is a superior alternative to existing treatments.

In an embodiment, the invention includes the use of at least one drug which is an α-aminoamide compound of formula (I):

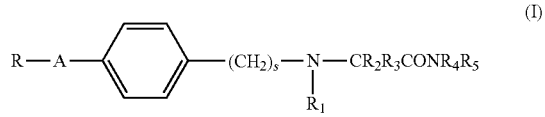

(I)

wherein:
A is a —$(CH_2)_n$—X— group, wherein n is an integer of 0 to 5, X is $CH_2$, —O—, —S— or —NH—;
s is 1 or 2;
R is a furyl, thienyl, or pyridyl ring or a phenyl ring, optionally substituted by one or two substituents independently selected from halogen, hydroxy, cyano, $C_1$-$C_6$ alkyl, $C_1$-$C_6$ alkoxy or trifluoromethyl;
$R_1$ is hydrogen or $C_1$-$C_6$ alkyl or $C_3$-$C_7$ cycloalkyl;
$R_2$ and $R_3$ are independently selected from hydrogen; $C_1$-$C_4$ alkyl, optionally substituted by hydroxy or phenyl; phenyl, optionally substituted by one or two substituents independently selected from $C_1$-$C_6$ alkyl, halogen, hydroxy, $C_1$-$C_6$ alkoxy or trifluoromethyl; or $R_2$ and $R_3$, taken with the carbon atom which they are linked to, form a $C_3$-$C_6$ cycloalkyl ring; and
$R_4$, $R_5$ are, independently, hydrogen, $C_1$-$C_6$ alkyl or $C_3$-$C_7$ cycloalkyl; or $R_4$ and $R_5$, taken together with the nitrogen atom they are linked to, form a 5-7 atom saturated heterocyclic ring;
or isomers, mixtures, and pharmaceutically acceptable salts thereof
for the preparation of a medicament for the treatment of the symptoms of Restless Leg Syndrome and addictive disorders.

The alkyl and alkoxy groups can be branched or can be straight chain groups.

Pharmaceutically acceptable salts of the compounds of the invention include, for example, acid addition salts with inorganic acids, e.g., nitric, hydrochloric, hydrobromic, sulfuric and phosphoric acids and the like, or organic acids, e.g., acetic, propionic, glycolic, lactic, oxalic, malonic, malic, tartaric, citric, succinic, benzoic, cinnamic, mandelic, methanesulfonic, p-toluenesulfonic and salicylic acids, and the like.

Some of the compounds of formula (I) can have asymmetric carbon atoms, and therefore can exist either as racemic mixtures or as individual optical isomers (enantiomers). Accordingly, the term "pharmaceutically acceptable salts" of the α-aminoamide of formula (I) is also meant to include within its scope all the possible isomers and their mixtures, and any pharmaceutically acceptable metabolite, bioprecursor and/or pro-drug, i.e., a compound which has a structural formula different from the one of the α-aminoamide of formula (I), and yet is directly or indirectly converted in vivo into a compound having formula (I), upon administration to a mammal, particularly a human being.

Preferred compounds of formula (I) are those wherein A is a group chosen from —$CH_2$—, —$CH_2$—$CH_2$—, —$CH_2$—S—, —$CH_2$—$CH_2$—S—, and —$(CH_2)_n$—O—, wherein n is an integer of 1 to 5;
s is 1 or 2;
R is a phenyl ring, optionally substituted by one or two substituents independently selected from halogen, trifluoromethyl, methoxy, or thienyl ring;
$R_1$ is hydrogen or $C_1$-$C_4$ alkyl;
one of $R_2$ and $R_3$ is hydrogen and the other is $C_1$-$C_4$ alkyl, optionally substituted by hydroxy or phenyl, optionally substituted by one or two halogen atoms, or $R_2$ and $R_3$ are both methyl, or together they can form with the atom they are linked to a cyclopropyl or a cyclopentyl ring; and
$R_4$, $R_5$ are hydrogen or $C_1$-$C_4$ alkyl, or, together with the nitrogen atom they are linked to, form a pyrrolidine or a piperidine ring, and the pharmaceutically acceptable salts thereof.

Examples of specific compounds of formula (I)—which can be used singly or in combination with other compounds of formula (I)—in an effective amount for treating RLS and addictive disorders in a patient include:
2-(4-Benzyloxybenzylamino)propanamide;
2-[4-(2-Methoxybenzyloxy)-benzylamino]propanamide;
2-[4-(2-Fluorobenzyloxy)-benzylamino]propanamide;
(S)-(+)-2-[4-(2-Fluorobenzyloxy)-benzylamino]propanamide
2-[4-(2-Fluorobenzyloxy)-benzylamino]-2-methyl-propanamide;
2-[4-(2-Fluorobenzyloxy)-benzylamino]-N-methyl-propanamide;
N-{2-[4-(2-Fluorobenzyloxy)-benzylamino]}propionyl-pyrrolidine;
2-[4-(3-Methoxybenzyloxy)-benzylamino]propanamide;
2-[4-(3-Cyanobenzyloxy)-benzylamino]propanamide;

2-[4-(3-Fluorobenzyloxy)-benzylamino]propanamide;
(S)-(+)-2-[4-(3-Fluorobenzyloxy)-benzylamino]propanamide;
2-[4-(3-Fluorobenzyloxy)-benzylamino]-2-methyl-propanamide;
2-[4-(3-Fluorobenzyloxy)-benzylamino]-N-methyl-propanamide;
N-{2-[4-(3-Fluorobenzyloxy)-benzylamino]}propionyl-pyrrolidine;
2-[4-(4-Fluorobenzyloxy)-benzylamino]propanamide;
2-[4-(3-Fluorobenzyloxy)-benzyl amino]-2-methyl-propanamide;
2-[4-(2-Chlorobenzyloxy)-benzylamino]propanamide;
2-[4-(3-Chlorobenzyloxy)-benzylamino]propanamide;
2-(4-Benzyloxybenzylamino)-3-hydroxy-propanamide;
2-[4-(2-Fluorobenzyloxy)-benzylamino]-3-hydroxy-propanamide;
2-[4-(3-Fluorobenzyloxy)-benzylamino]-3-hydroxy-propanamide;
2-(4-Benzyloxybenzylamino)-3-hydroxy-N-methyl-propanamide;
2-[4-(2-Fluorobenzyloxy)-benzylamino]-3-hydroxy-N-methyl-propanamide;
2-[4-(3-Fluorobenzyloxy)-benzylamino]-3-hydroxy-N-methyl-propanamide;
2-[4-(2-Chlorobenzyloxy)-benzylamino]-3-hydroxy-N-methyl-propanamide;
2-[4-(3-Cyanobenzyloxy)-benzylamino]-3-hydroxy-N-methyl-propanamide;
2-[4-(3-Cyanobenzyloxy)-benzylamino]-2-methyl-3-hydroxy-N-methyl-propanamide;
2-[4-(3-Chlorobenzyloxy)-phenylethylamino]propanamide;
2-{4-[2-(3-Fluorophenyl)-ethyloxy]benzylamino}propanamide;
2-{4-[2-(3-Fluorophenyl)-ethyl]benzylamino}propanamide;
2-[N-(4-Benzyloxybenzyl)-N-methylamino]propanamide;
2-{4-[(3-Chlorobenzyloxy)-phenylethyl]-amino}propanamide;
2-[4-Benzylthiobenzylamino]propanamide;
2-[4-(2-Fluorobenzylthio)-benzylamino]propanamide;
2-[4-(3-Fluorobenzylthio)-benzylamino]propanamide;
2-[4-(3-Phenylpropyloxy)-benzylamino]propanamide;
2-[4-(4-Phenylbutyloxy)-benzylamino]propanamide;
2-[4-(5-Phenylpentyloxy)-benzylamino]propanamide;
2-(4-Benzyloxybenzylamino)-3-phenyl-N-methyl-propanamide;
2-(4-Benzyloxybenzylamino)-3-methyl-N-methyl-butanamide;
2-(4-Benzyloxybenzylamino)-2-phenyl-acetamide;
2-[4-(2-Fluorobenzyloxy)-benzylamino]-2-phenyl-acetamide;
2-[4-(3-Fluorobenzyloxy)-benzylamino]-2-phenyl-acetamide;
2-[4-(2-Fluorobenzyloxy)-benzyl-N-methylamino]-2-phenyl-acetamide;
2-[4-(3-Fluorobenzyloxy)-benzyl-N-methylamino]-2-phenyl-acetamide;
2-[4-(3-Chlorobenzyloxy)-benzylamino]-2-phenyl-acetamide;
2-[4-(2-Fluorobenzyloxy)-benzylamino]-2-(2-fluorophenyl)-acetamide;
2-[4-(2-Fluorobenzyloxy)-benzylamino]-2-(3-fluorophenyl)-acetamide;
2-[4-(3-Fluorobenzyloxy)-benzylamino]-2-(2-fluorophenyl)-acetamide;
2-[4-(3-Fluorobenzyloxy)-benzylamino]-2-(3-fluorophenyl)-acetamide;
2-[4-(3-Chlorobenzyloxy)-benzylamino]-2-(3-fluorophenyl)-acetamide;
2-(4-(2-Thienyloxy)-benzylamino)propanamide;
or isomers, mixtures, and pharmaceutically acceptable salts thereof.

Preferred compounds of formula (I), which can be used singly, or in combination with other compounds of formula (I), in an effective amount for treating one or more RLS or addictive disorders symptoms in a patient are (S)-(+)-2-[4-(2-Fluorobenzyloxy)-benzylamino]propanamide or (S)-(+)-2-[4-(3-Fluorobenzyloxy)-benzylamino]propanamide.

In one embodiment the patient being treated is a mammal, including humans, in need of alleviation, or inhibition of symptoms of one or more RLS or addictive disorders symptoms.

Particularly, the mammal in need of the above mentioned treatment is administered a dose of an α-aminoamide of formula (I) as above defined which ranges from about 0.3 to about 100 mg/kg of body weight per day. "Treatment" as used herein includes any care by procedures or applications to a mammal, and particularly a human, that are intended to a) prevent the disease or disorder from occurring in a subject that may be predisposed to the disease/disorder, but has not yet been diagnosed with having it; b) inhibiting the disease/disorder, or condition, i.e., arresting its development; or c) relieving the disease/disorder, or condition, i.e., causing regression of the disease/disorder, or condition.

RLS and additive disorders condition in a mammal, including humans, can thus be inhibited or alleviated.

Examples of RLS symptoms are motor restlessness, creeping, burning or pulling sensations deep in the legs, between the knees and the ankles. Sleepiness and sleep disturbances are direct consequences of the previous described symptoms.

Examples of addictive disorders are drug abuse, severe alcoholism, reward deficiency syndrome (RDS).

In another aspect, the invention includes an α-aminoamide of formula (I) administered as the active agent of a pharmaceutically acceptable composition having activity in the treatment of RLS and addictive disorders which can be prepared by conventional procedures, for instance by mixing the active agent with a pharmaceutically acceptable, therapeutically inert organic and/or inorganic carrier or excipient materials.

Preferred compounds of formula (I), used in an effective amount for treating RLS and addictive disorders in a patient are (S)-(+)-2-[4-(2-fluorobenzyloxy)-benzylamino]propanamide or (S)-(+)-2-[4-(3-fluorobenzyloxy)-benzylamino]propanamide. The compounds of formula (I), and the pharmaceutically acceptable salts thereof, may be obtained by well known processes as described in the patent applications cited above.

Combination therapy" (or "co-therapy") includes the administration of an alpha-aminoamide compound of formula (I) of the invention and at least a second agent, for example:
    dopamine agonists such as bromocriptine, cabergoline, lisuride, pergolide, ropinirole, apomorphine, sumanirole, rotigotine, talipexole, dihydroergocriptine and pramipexole,
    levodopa, levodopa plus carbidopa (SINEMET®), levodopa plus controlled release carbidopa (SINEMET-CR®), levodopa plus benserazide (MADOPAR®), levodopa plus controlled release benserazide (MADOPAR-HBS), COMT inhibitors such as tolcapone and entacapone, STALEVO®, Amantadine and anticholinergic agents, as part of a specific treatment regimen intended to provide the beneficial effect from the co-action of these therapeutic agents. Benefits of such combinations include reduction of the dose of conventional agents (i.e., other than the agents of the present invention) with consequent reduction of the side-effects of such conventional agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations contemplated by the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The α-aminoamide compositions of the invention can be administered in a variety of dosage forms, e.g., orally, in the form of tablets, troches, capsules, sugar or film coated tablets, liquid solutions, emulsions or suspensions; rectally, in the form of suppositories; parenterally, e.g., by intramuscular or intravenous injection or infusion; and transdermally in the form of a patch, ointment, emulsion, lotion, solution, gel, cream and nasal spray.

Suitable pharmaceutically acceptable, therapeutically inert organic and/or inorganic carrier or excipient materials useful in the preparation of such composition include, for example, water, gelatin, gum arabic, lactose, starch, cellulose, magnesium stearate, talc, vegetable oils, cyclodextrins, polyalkyleneglycols and the like. The α-aminoamide compositions of formula (I) can be sterilized and may contain further components, well known to those skilled in the art, such as, for example, preservatives, stabilizers, wetting or emulsifying agents, e.g., paraffin oil, mannide monooleate, salts to adjust osmotic pressure, buffers and the like.

Additionally, the solid oral forms can contain, together with the active agent, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gums, gelatin, methylcellulose, carboxymethylcellulose or polyvinyl pyrrolidone; disaggregating agents, e.g., a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. The pharmaceutical preparations may be manufactured in any known manner, for example, by means of mixing, granulating, tabletting, sugar-coating, or film-coating processes.

The oral formulations comprise sustained release formulations which can be prepared in a conventional manner, for instance by applying an enteric coating to tablets and granules.

The liquid dispersion for oral administration may be e.g., syrups, emulsions and suspension. The syrups may further contain as a carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethyl-cellulose, or polyvinyl alcohol. The suspensions or solutions for intramuscular injections may contain, together with the active compound, a pharmaceutically acceptable carrier, e.g., sterile water, olive oil, ethyl oleate, glycols, e.g., propylene glycol, and, if desired, a suitable amount of lidocaine hydrochloride. The solutions for intravenous injections or infusion may contain as a carrier, for example, sterile water or preferably they may be in the form of sterile, aqueous, or isotonic saline solutions.

The suppositories may contain, together with the active agent, a pharmaceutically acceptable carrier, e.g., cocoa butter, polyethylene glycol, a polyoxyethylene sorbitan fatty acid ester surfactant or lecithin.

Compositions including α-aminoamides of formula (I) are generally in the form of a dose unit containing, for example, 20 to 7000 mg of active ingredient per unit dosage form. Suitable treatment is given 1 or 2 or 3 times daily, depending upon clearance rate. Accordingly, the desired dose may be presented in a single dose or as divided doses administered at appropriate intervals, for example, two to four or more sub-doses per day.

The pharmaceutical compositions including an α-aminoamide of formula (I) can contain, per dosage unit, e.g., capsule, tablet, powder injection, teaspoonful, suppository and the like, from about 20 to 7000 mg of the active agent.

Optimal therapeutically effective doses to be administered may be readily determined by those skilled in the art and will vary, basically, with the strength of the preparation, with the mode of administration and with the advancement of the inflammatory condition or disorder treated. In addition, factors associated with the particular subject being treated, including subject age, weight, diet and time of administration, will result in the need to adjust the dose to an appropriate therapeutically effective level.

The advantages derived from the uses and the methods of the invention as above defined are many, and include the possibility to treat basically all types of RLS and addictive disorders symptoms.

EXAMPLE 1

Open Label RLS Study

In an open label study conducted on 10 patients with idiopathic RLS, 2 week administration of (S)-(+)-2-[4-(3-Fluorobenzyloxy)-benzylamino]-propanamide 100 mg/die resulted efficacious in improving RLS symptoms. Patients were included in the study if they fulfilled the minimal diagnostic criteria according to the International RLS Study Group. Patients' symptoms had to interfere with sleep onset or maintenance for at least 6 months and at least 15 nights during the last 12 weeks, and they should have IRLS 10 (International Restless Legs Syndrome) score equal to or greater than 15 at baseline assessment. Physical examination, biochemical and haematological laboratory tests and electrocardiogram were performed to ensure that selection criteria were fulfilled. Polysomnography was performed for 2 nights at baseline and 2 nights at the end of treatment, in order to verify the effects of (S)-(+)-2-[4-(3-Fluorobenzyloxy)benzylamino]propanamide on sleep. Efficacy was measured through the following evaluation scales: International Restless Legs Syndrome 10 (IRLS 10), Restless Legs Syndrome Quality of Life (RLS QoL), Work Productivity and Activity Impairment Questionnaire (WPAI RLS) and Clinical Global Impression (CGI part I and CGI part II).

Patients treated with (S)-(+)-2-[4-(3-Fluorobenzyloxy)-benzylamino]-propanamide shown a significant improvement in RLS symptoms.

Comparing the after 2 weeks treatment score with baseline one, a decrease rate tendency is shown in all considered evaluation scales.

In this group of patient (S)-(+)-2-[4-(3-Fluorobenzyloxy)-benzylamino]propanamide was well tolerated and no adverse events were registered.

Results

The 10 patients enrolled in the study demonstrated a significant improvement in all the evaluation scales used.

Ten out of 10 patients enrolled were considered eligible for the efficacy analysis; all of them completed the planned period of treatment of 14+3 days. Baseline values for demography showed a 70% of female enrolled and an average age of 61.30 years, with very few concomitant baseline diseases, and no abnormalities at the physical examination. As to the main disease, it was considered severe in 70% of patients according to CGI criteria and confirmed by IRLS-10 score, with an impact on daily activity, that could be quantified (according to WPAI-RLS, and RLS-QoLQ results) in about ⅓ of the usual performances. PSG registration suggested a disease effect on sleep, as testified by baseline values of PLM Arousal Index of 8.90, Sleep Efficiency 72.62, and number of awakenings during sleep.

CGI part I had an impressive improvement in disease situation in 60% of patients with stable disease in the other 40% (FIG. 1). These changes achieved statistical significance ($P=0.031$).

CGI part II had an improvement of any grading in 90% of patients, and only one 1 patient (10%) has been considered to have no changes (see table I).

TABLE I

CGI part II changes from previous visit.

| Score | | | Total |
|---|---|---|---|
| Final | Very Much Improved | N (%) | 2 (20) |
| | Much Improved | N (%) | 2 (20) |
| | Minimally Improved | N (%) | 5 (50) |
| | No change | N (%) | 1 (10) |

IRLS-10 scale had statistically significant improvement of total score ($p=0.002$) with score reduction in all the patients; this improvement has been confirmed in the analysis of sub-items by improvement of "diagnostic features" ($p=0.002$) and "disease impact" ($p=0.003$) reaching the statistical significance, and by those of "associated features", and "severity" close to significance (tab II).

TABLE II

IRLS 10 Score

| Parameter | | Visits Baseline | Final | P (t test) |
|---|---|---|---|---|
| Total Score | mean | 27.50 | 21.80 | |
| | SD | 4.33 | 4.80 | |
| | changes | | −5.70 | 0.002 |
| Diagnostic Features | mean | 11.20 | 8.50 | |
| | SD | 1.75 | 1.51 | |
| | changes | | −2.70 | 0.002 |
| Associated Features | mean | 5.10 | 4.30 | |
| | SD | 1.66 | 1.34 | |
| | changes | | −0.80 | 0.070 |
| Severity | mean | 7.00 | 6.00 | |
| | SD | 0.82 | 1.41 | |
| | changes | | −1.00 | 0.063 |
| Impact | mean | 4.20 | 3.00 | |
| | SD | 1.62 | 1.56 | |
| | changes | | −1.20 | 0.003 |

RLS-QoLQ had a significant decrease in the total score ($p=0.002$) as shown in FIG. 2.

WPAI-RLS had an improvement in the item 6 which gives suggestion of improvement observed on ability of patients to conduct their daily activities; in fact there was a statistically significant reduction ($p=0.005$) of the impairment from 34% to 22% as shown in FIG. 3.

Polysomnographic registration (PSG) had statistically significant improvement versus baseline in PLM (Wake+Sleep) Index, PLM Wake Index, PLM Sleep Index and by trend in the other PSG parameters, without overall sleep architecture modification as shown in FIG. 4, FIG. 5, FIG. 6.

In conclusion, this trial revealed that (S)-(+)-2-[4-(3-Fluorobenzyloxy)-benzylamino]propanamide has a good safety profile and provided evidence of an improvement observed in the disease and its clinical manifestations. This evidence has been fortified by objective instrumental measure of disease correlates (i.e. PSG).

For addiction studies some animal models were used to test the efficacy of test compounds. In particular the following tests were performed. The test compounds were found to decrease the behavioural effect of some drug of abuse in different animal models, demonstrating potential therapeutic effect in addictive disorder.

EXAMPLE 2

Cocaine Interaction Study in Mice

Typically, psychostimulant addictive drugs as amphetamine and cocaine induce an increase in locomotor activity in rodents and primate. Some compounds with anti-addictive potential properties can prevent the increase in locomotor activity induced by psychostimulant drugs. (Katz J L, Kopajtic T A, Myers K A, Mitkus R J, Chider M, Behavioral effects of cocaine: interactions with D1 dopaminergic antagonists and agonists in mice and squirrel monkeys. J Pharmacol Exp Ther. 1999 Oct; 291(1):265-79).

The effect of test compounds is evaluated in a mice model of cocaine-induced locomotion increase.

Method

Subjects: Swiss-Webster Mice, male

Apparatus: Automated photocell chambers

Drugs: Cocaine 20 mg/kg is administered ip, test compounds dissolved in vehicle are administered ip at different doses (10-100 mg/kg) right before cocaine.

Behavioral test: Animals (8 per experimental group) received ip injection of cocaine (20 mg/kg) or saline and either the test compounds (10-100 mg/kg ip) or their vehicle and locomotor activity is recorded for 1 hour.

Data Analysis

Time Course: For vehicle, cocaine alone, and each dose of test compound alone+cocaine the mean (+SEM) activity for each 10 min period is plotted.

Maximal effect: The 30 min time period in which cocaine (20 mg/kg) produces the maximal activity is used to determine test compound effect. A log 10 transformation of the 30 min period average counts for individual subjects is performed in order to homogenize variances for subsequent analyses. An ANOVA statistical analysis is performed and vehicle and each dose of the test compound+cocaine to cocaine alone is compared to determine significant ($p<0.05$) dose effects. A linear least-squares regression analysis is conducted; the 30 min period average counts is regressed across subjects over the descending portion of the curve against the log 10 dose of the test compound. The AD50 (dose that attenuates cocaine-induced stimulation by 50%) is determined from the linear regression analysis.

EXAMPLE 3

Rat Drug Discrimination Assay

The Drug Discrimination (DD) Tasks is a procedure for the evaluation of the capacity of a compound to substitute for a psychoactive drug (such as drug of abuse). The rat learns to utilize interoceptive drug stimuli to signal which of two or three manipulanda will produce food deliveries (state-dependent learning). Such tasks constitute the best animal model to examine "subjective" drug effects. Additionally, DD procedures may have the capability in certain instances to independently measure several different subjective effects of a drug, including some which promote drug abuse (euphorigenic) and others that deter drug abuse (nocioceptive).

The potentiating or preventing effects on drug abuse of the test compounds are evaluated in a model of cocaine discrimination test in rats.

(Colpaert FC (1986) Drug discrimination: behavioral, pharmacological and molecular mechanisms of discriminative drug effects, in Behavioral Analysis Of Drug Dependence, Goldberg S R and Stolerman I P eds, pp 161-193, Academic Press, Orlando).

Methods

Subjects. Studies in male Sprague-Dawley rats are conducted. All animals are housed in a temperature- and humidity-controlled vivarium with a 12-h light/dark cycle (lights on 7:00 AM). All experiments are conducted during the light phase of the light/dark cycle, between 8:00 AM and 3:00 PM. The rats were maintained at approximately 80-85% ad lib body weight.

Cocaine Discrimination. Rats are fed daily about 15 g of standard lab chow at least 30 min after testing that maintained them at their individual weights throughout the study. Subjects are tested daily in two-lever operant-conditioning chambers that are housed within light- and sound-attenuating enclosures. White noise is present throughout testing to mask extraneous sounds. Ambient illumination is by a lamp in the top center of the front panel (house light). Levers are set 17 cm apart, with pairs of lamps (light-emitting diodes; LEDs) above each of the levers, also on the front panel. Reinforced responses dispense one 45-mg pellet into a food tray centered between the levers on the front panel of the chamber. Subjects are initially trained to press both levers under a 10-response fixed ratio (FR 10) schedule of food reinforcement and to discriminate i.p. injections of 29 μmol/kg cocaine (10 mg/kg) from i.p. injections of saline. After cocaine injection, responses on only one lever are reinforced; after saline injection, responses on the other lever are reinforced. The assignment of cocaine- and saline-appropriate levers was counterbalanced across rats. Immediately after injection, rats are placed inside the experimental chambers. A 5-min time-out period, during which the house light and LEDs are extinguished and responding had no scheduled consequences precede the illumination of the house light and the LEDs. Only responses on the appropriate lever are reinforced, and responses on the inappropriate lever reset the FR response requirement. Each food presentation is followed by a 20-s time-out period during which all lights are off, and responding has no scheduled consequences. Sessions end after 20 food presentations or 20 min, whichever occurs first. Training sessions with cocaine (C) and saline (S) injections are conducted daily 5 days per week and order in a double alternation sequence (e.g., SCCS).

Testing is initiated when performances reach criteria of at least 85% appropriate responding overall and during the first FR 10 of the session over four consecutive sessions. Selected doses of the test compounds were administered po at different times up to 360 min after injection to examine the time course of the discriminative-stimulus effects. After a test session, a subject is required to meet the above-mentioned performance criteria over two consecutive (cocaine and saline) training sessions to be tested again. Repeated test sessions are conducted, with at least two training sessions between tests, until entire dose-effects are determined in each subject. Test sessions are identical to training sessions, with the exception that 20 consecutive responses on either lever are reinforced.

For each of the rats studied in the cocaine-discrimination procedure, the overall response rate and the percentage of responses occurring on the cocaine-appropriate lever are calculated. The mean values are calculated for each measure at each drug dose tested. If less than one-half of the rats responded at a particular dose, no mean value is calculated for percentage of cocaine-appropriate responding at that dose. At least 20% cocaine-appropriate responding is adopted as a conservative criterion at which to assume a significant difference from saline; 80% or higher cocaine-appropriate responding is taken as similar to the training dose of cocaine, and intermediate levels of cocaine-appropriate responding are considered partial substitution.

Data Analyses. Results of cocaine discrimination studies are assessed with data collected during the entire session, which last a maximum of 20 min.

If and individual subject does not complete one fixed-ratio schedule during testing, its data are included in the average for response rate, but not included in the average for percent cocaine-lever responding. An ED50 value is calculated using linear regression analysis for those test compounds that substitute for cocaine (>80% drug-appropriate responding). For those test compounds that substitute partially (>20% and <80% drug appropriate responding) for cocaine, the lowest dose that produces maximum substitution and what percentage is given. For those compounds that do not substitute for cocaine (<20% drug appropriate responding), the highest dose tested is calculated.

EXAMPLE 4

Rat Drug Self-Administration Test

Drug Self-Administration test is a widely used method to study the reinforcing properties of a drug (such as cocaine) and the effects of various compounds on these rewarding properties. In this test the rat is trained to "work" in order to receive oral or intravenous administration of drugs. This behavioral method permits to asses if a test compound has an effect on the reinforcing properties of an addictive drug. (Caine S. B.; Lintz R; Koob G. F.: Intravenous drug self-administration techniques in animals. In: Behavioral Neuroscience: A Practical Approach. ed. by A. Sahgal pp 117-143, Oxford University Press, New York. 1993; Fischman M W, Behavioral pharmacology of cocaine J. Clin Psychiatry. February 1988; 49 Suppl: 7-10).

Method

Subjects

Male Sprague—Dawely rats, weighing 350-400 g are housed 3 to a cage and provided with ad libitum access to food and water and maintained on a 12-h light-dark cycle (lights on 7:00 am-7:00 pm).

Self-Administration

All animals are surgically implanted with a chronic silastic jugular vein catheter under ketamine (60 mg/kg IP) and sodium pentobarbital (20 mg/kg ip) anesthesia. The catheter passed subcutaneously to an exposed portion of the skull where it is affixed with dental acrylic to four stainless steel screws embedded in the skull. At the time of the self-administration session (normally 6 days per week), the catheter is connected to a swivel system through a metal spring, which is in turn connected to an infusion pump.

Seven days following surgery, the animals are allowed 2-h access each day to a metal lever mounted on the side wall of a standard operant-conditioning cage, 3 cm from the cage floor. The force requirement to press the lever is an average of 30 grams (a range of 25 to 35 grams in different cages). The cages themselves are housed inside sound attenuated chambers. Two levers are present in each operant chamber, one lever resulted in a drug infusion, while the other remained inactive throughout all sessions. An active lever press resulted in an intravenous injection of 0.1 ml of cocaine hydrochloride (0.50 mg/kg/injection) dissolved in 0.9% physiological saline and delivered over a period of 4 s. A swivel system allows free movement of the animal in the cage. Coincident with the onset of the injection, a stimulus light located 1 cm above the lever on the same side wall of the operant chamber is turned on for 20 s during which time the lever became inactive. Lever presses during the period when the signal light is not lit were reinforced on a continuous reinforcement schedule (fixed ratio 1, FR-1). Once the animals demonstrated stable drug intake for three days (a range of less than 15% of the daily intake over three days), the self-administration schedule is switched to an FR10 until stabilization (15-20 days) and then the study starts. On a test day, the animals are pre-treated ip immediately before the beginning of the session with the test compound. Different doses of test compound are used. Each dose is tested only once for each animal using a Latin-square design. At least two days of baseline self-administration separate drug testing days.

Data Analysis

The total number of reinforcers earned during the 120-min session is recorded and statistical analysis of the data is computed using a one-way factorial analysis of variance with repeated measures (ANOVA) or Student's t-test where appropriate. Individual means comparisons are made using a Newman-Keuls a posteriori test.

EXAMPLE 5

Cocaine-Induced Behavioral Sensitization in Rats

Drug addiction is a pathological behaviour characterized by compulsive drug seeking and intake. One animal model of these behavioural changes is the long-lasting increase in locomotor activity induced by repeated administration of psychostimulant drugs in rodents (Robinson et al., 1993) known as drug-induced behavioural sensitization. The effect of test compounds are evaluated in a model of cocaine-induced behavioral sensitization in rat.

Method

Subjects. Male Wistar rats weighing 200-250 g upon arrival are used.

Locomotor activity apparatus. Locomotor activity is measured in sixteen identical metal wire hanging cages each measuring 36 cm (L)×25 cm (W)×20 cm (H). Each cage contained two sets of infrared emitter-detector photocells positioned along the long axis 1-cm above the grid floor and 8 cm from the front and back of the cage. Background noise is provided by a white noise generator. Movement within the cages produced photocell interruptions, which are automatically recorded by an IBM-compatible computer.

Sensitization procedure and treatment. Animals are habituated to the locomotor activity chambers for 2-3 consecutive days before the experiment. Rats receive 5 daily ip injections of cocaine (15 mg/kg) or saline and either the test compound (40-100 mg/kg ip) or its vehicle and locomotor activity is recorded for 3 hours. Ten days after the last injection of cocaine or saline (day 15), the animals are challenged with 15 mg/kg of cocaine in absence of the test compound and locomotor activity is again monitored for 3 h.

By the fifth day of treatment with cocaine, animals pretreated ip with vehicle showed an increased locomotor response (20% higher then the first day, $p<0.05$). Ten days after the last injection of cocaine or saline, the animals are challenged with 15 mg/kg of cocaine in absence of the test compound and locomotor activity is again monitored for 3 h. The rats previously treated with cocaine and that have not received the test compound are expected to show an increased locomotor activity response to cocaine (30% higher then first day, $p<0.05$). If the rats that had been pre-treated with the test compound during the 5 day-cocaine treatment did not show an increase in locomotor activity the test compound is considered to have an effect in preventing psychostimulant drugs addiction. (Koob, G. F., Sanna, P. P. & Bloom, F. E. *Neuron* 21, 467-476 1998; Robinson T. E. & Berridge K. C. The neural basis of drug craving: an incentive-sensitization theory of addiction. *Brain Res Brain Res Rev* 18, 247-91, 1993)

Data analysis. Data (total number of beam breaks in 3 hours) are analyzed using a two way ANOVA with repeated measures on one factor including the four experimental groups (i.e., saline/vehicle, saline/test compound, cocaine/ vehicle and cocaine/test compound) and two time points (day 1 and day 5) followed by a simple effects analysis. A second two way ANOVA with repeated measures on one factor is used to compare day 1 and the challenge day followed by a Newman-Keuls post hoc test.

EXAMPLE 6

Monkey Drug Discrimination Assays

Cocaine discrimination is a behavioral assay extensively used to evaluate candidate treatment medications. The potency and time course of the cocaine-like behavioral effects produced by an acute administration of the test compound are determined in this procedure. Specifically, the test compound is administered either alone or as a pretreatment to cocaine in rhesus monkeys trained to discriminate 0.4 mg/kg cocaine from saline.

Method

Subjects. The subject are adult male rhesus monkeys (*Macaca mulatta*). Monkeys are maintained on a diet of 3-4 monkey biscuits (Purina Monkey Chow Jumbo #5037) and one piece of fresh fruit per day in addition to fruit-flavored pellets delivered during operant sessions. Water is freely available for all monkeys at all times. The monkeys are housed in a humidity and temperature controlled room with 12 hr light-dark cycle (light on from 7 am to 7 pm).

Apparatus. Each monkey is housed individually in a well-ventilated, stainless steel chamber (56×71×69 cm). The home cages of all monkeys are modified to include an operant panel (28 3 28 cm) mounted on the front wall. Three square translucent response keys (6.4×6.4 cm) are arranged 2.54 cm apart in a horizontal row 3.2 cm from the top of the operant panel. Each key can be transilluminated by red or green stimulus lights (Superbright LEDs). The operant panel also support an externally mounted pellet dispenser (Gerbrands, Model G5210) that deliver 1-g food pellets to a food receptacle mounted on the cage beneath the operant response panel. Operation of the operant panels and data collection are accomplished with a computer located in a separate room.

Discrimination Training. Drug discrimination procedures are similar with those used in other studies (Lamas X, Negus S S, Hall E and Mello N K (1995) relationship between the discriminative stimulus effects and plasma concentrations of intramuscular cocaine in rhesus monkeys. *Psychopharmacology* 121:331-338; Negus S S, Mello N K, Portoghese P S, Lukas S E and Mendelson J H (1995) Role of delta opioid receptors in the reinforcing and discriminative stimulus effects of cocaine in rhesus monkeys. *J Pharmacol Exp Ther* 273:1245-1256.; Negus S S, Mello N K, Lamas X and Mendelson J H (1996) Acute and chronic effects of flupentixol on the discriminative stimulus and reinforcing effects of cocaine in rhesus monkeys. *J Pharmacol Exp Ther* 278:879-890.

Discrimination sessions consist of multiple cycles and are conducted 5 days/week. Each cycle consisted of a 15-min time-out period followed by a 5-min response period. During the time-out, all stimulus lights are off and responding had no scheduled consequences. During the response period, the right and left response keys are trans-illuminated red or green, and monkeys can receive up to 10 food pellets by responding under a fixed ratio (FR) 30 schedule of food presentation. For a group of monkeys, the left key is illuminated green and the right key is illuminated red. For the other group of monkeys, the colours of the response keys are reversed. The center key is not illuminated at any time, and responding on the center key has no scheduled consequences. If all available food pellets are delivered before the end of the 5-min response period, the stimulus lights trans-illuminating the response keys are turned off, and responding has no scheduled consequences for the remainder of that response period. On training days, monkeys are given an i.m. injection of either saline or 0.40 mg/kg cocaine 5 min after the beginning of each time-out period (i.e., 10 min before the response period). After administration of saline, responding on only the green key (the saline appropriate key) produce food, whereas following administration of 0.40 mg/kg cocaine, only responding on the red key (the drug-appropriate key) produce food. Responses on the inappropriate key reset the FR requirement on the appropriate key. Daily sessions consist of one to five cycles, and if the training dose of cocaine is administered, it is administered only during the last cycle. Thus, training days consist of 0-5 saline cycles followed by 0-1 drug cycles.

During the response period of each cycle, three dependent variables are determined: 1) percentage of injection-appropriate responding before delivery of the first reinforcer [(injection-appropriate responses emitted before 1st reinforcer/total responses emitted before 1st reinforcer)×100]; 2) percentage of injection appropriate responding for the entire response period [(injection-appropriate responses emitted during response period/total responses emitted during response period)×100]; and 3) response rate (total responses emitted during response period/total time stimulus lights were illuminated). Monkeys are considered to have acquired cocaine discrimination when the following three criteria are met for seven of eight consecutive training sessions: 1) the percentage of injection-appropriate responding before delivery of the first reinforcer is greater than or equal to 80% for all cycles; 2) the percentage of injection-appropriate responding for the entire cycle is greater than or equal to 90% for all cycles; and 3) at least one pellet is earned during all training cycles.

Discrimination Testing. Once monkeys met criterion levels of cocaine discrimination, testing begin. Test sessions are identical with training sessions except that responding on either key produced food, and cocaine or test compounds are administered as described below. Two series of experiments are conducted to characterize the effects of test compound administered alone or as a pretreatment to cocaine. In the first series of experiments, the time course of the effects of the test compound alone are determined. A single dose of the test compound (1-100 mg/kg) is administered at the beginning of the test session, and 5 min response periods begin after 10, 30, 100, and 300 min. In the second series of experiments, the effects of the test compound pretreatment on cocaine discrimination are determined. A single dose the test compound is administered at an appropriate time before a test session in which a cumulative cocaine dose-effect curve is determined (0.013-1.3 mg/kg). In general, the test drug is evaluated up to doses that either produce a significant change in cocaine dose-effect curve, or decrease response rates to less than 0.1 responses/sec averaged over the entire session.

Data Analysis. The percentage of cocaine-appropriate responding (for the entire response period) and response rates are plotted as a function of either the time after test compound administration (for time-course studies) or the cumulative dose of cocaine (for test compound pre-treatment studies). A percentage of cocaine-appropriate responding for a given cycle was included in the analysis only if the monkey emit at least 30 responses during the cycle (i.e., enough responses to result in the delivery of one reinforcer). ED50 values are defined as the dose of test compound or cocaine that produce 50% cocaine-appropriate responding, and are calculated by linear interpolation from individual subject dose-effect curves. For each test compound, ED50 values are calculated from data obtained at the approximate time of peak effect.

EXAMPLE 7

Monkey Drug Self-Administration Test

Self-administration procedures in laboratory animals are often used to evaluate candidate medications for managing addiction to cocaine and related psychomotor stimulant drugs. Usually, experiments are conducted to determine how drugs alter response rates or the number of i.v. injections under a single schedule, with reinforcement consequent to a fixed or progressively increasing number of responses, i.e., fixed ratio (FR) or progressive ratio schedules (Mello N K and Negus S S (1996) Preclinical evaluation of pharmacotherapies for treatment of cocaine and opioid abuse using drug self administration procedures. *Neuropsychopharmacology* 14:375-424). In such research, the comparison of changes in i.v. self-administration behavior and performance maintained by another reinforcer such as food delivery can provide a measure of behavioral selectivity in the effects of a candidate medication (Woolverton W L (1996) Intravenous self-administration of cocaine under concurrent VI schedules of reinforcement. *Psychopharmacology* 127:195-203.; Negus S S, Brandt M R, and Mello N K (1999) Effects of the long-acting monoamine reuptake inhibitor indatraline on cocaine self-administration in rhesus monkeys. *J Pharinacol Exp Ther* 291:60-69; Caine S B, Negus S S, and Mello N K (2000) Effects of dopamine D1-like and D2-like agonists on cocaine self-administration in rhesus monkeys: rapid assessment of cocaine dose-effect functions. *Psychopharmacology* 148:41-51).

Method

Subjects. The subject are adult male rhesus monkeys (*Macaca mulatta*). Monkeys are maintained on a diet of 3-4 monkey biscuits (Purina Monkey Chow Jumbo #5037) and one piece of fresh fruit per day in addition to fruit-flavored pellets delivered during operant sessions. Water is freely available for all monkeys at all times. The monkeys are housed in a humidity and temperature controlled room with 12 hr light-dark cycle (light on from 7 am to 7 pm).

Surgical procedures. Double-lumen Silicone rubber catheters (i.d. 0.7 mm; o.d. 2.0 mm) were implanted in the jugular or femoral vein and exited in the midscapular region. All surgical procedures are performed under aseptic conditions. Monkeys are initially sedated with ketamine (5 mg/kg), and anesthesia is induced with sodium thiopental (10 mg/kg, i.v). In addition, monkeys are treated with 0.05 mg/kg atropine to reduce salivation. Following insertion of tracheal tube, anesthesia is maintained with isoflurane (1-1.5% in oxygen). After surgery, aspirin or acetaminophen (80-160 mg/day, p.o.) is administered for 3 days. An antibiotic, procaine penicillin G (300,000 U/day, i.m.), is administered every day for 5 days. The i.v. catheter is protected by a tether system consisting of a custom fitted nylon vest connected to a flexible stainless steel cable and fluid swivel (Lomir Biomedical, Malone, N.Y.). This flexible tether system permitted monkeys to move freely. Catheter patency is periodically evaluated by i.v. administration of a short-acting barbiturate, methohexital (3 mg/kg, i.v.). The catheter is considered to be patent if i.v. administration of methohexital produced a loss of muscle tone within 10 s.

Behavioral apparatus. Each monkey is housed individually in a well ventilated stainless steel chamber (64×64×79 cm). The home cages of all monkeys are modified to include an operant panel (28×28 cm) mounted on the front wall. Three square translucent response keys (6.4×6.4 cm), are arranged 2.54 cm apart in a horizontal row 3.2 cm from the top of the operant panel. Each key can be transilluminated by red or green stimulus lights (Superbright LED's). The operant panel also supports an externally-mounted pellet dispenser that delivers 1 g fruit-flavored food pellets to a food receptacle mounted on the cage beneath the operant response panel. In addition, two syringe pumps (model B5P-IE; Braintree Scientific, Braintree, Mass., or model 980210; Harvard Apparatus, South Natick, Mass.) are mounted above each cage for delivery of saline or drug solutions through the two lumen of the i.v. catheters. Operation of the operant panels and data collection were accomplished with a computers located in a separate room.

Initial Training Procedures. Procedures for the evaluation of cocaine- and food-maintained responding were similar to those used in other studies (Negus S S, Mello N K, Portoghese P S and Lin C E (1997) Effects of kappa opioids on cocaine self-administration by rhesus monkeys. *J Pharmacol Exp Ther* 282: 44-55; Negus S S, Mello N K, Portoghese P S, Lukas S E and Mendelson J H (1995) Role of delta opioid receptors in the reinforcing and discriminative stimulus effects of cocaine in rhesus monkeys. *J Pharmacol Exp Ther* 273:1245-1256.). Under a basic protocol, food and iv injections are available during three alternating component. Both food and iv injections are available under a FR30 schedule of reinforcement. A red light is associated with food delivery and a green light is associated to drug injections. The food and drug component are separated by a 5-min time out. The entire food-drug-food session lasts 120 min and is conducted daily from 3-5 pm. During training the solution available for self-administration during the drug component is alternated between 0.032 mg/kg/inj cocaine and saline. Monkeys are trained until they meet the following criteria for stable cocaine self-administration: 1) 3 consecutive days during which the response rate during the drug component of each session differ by no more than 20% from the mean drug component response rate; 2) rapid saline extinction as indicated by a decrease in drug component response rates on the first day of saline substitution.

Drug Self-Administration Testing. Once monkeys met the criteria for high stable levels of cocaine and food self-administration, testing is initiated using substitution sessions in which different doses of cocaine (0.00032-0.1 mg/kg/injection) are substituted for the saline/cocaine training dose conditions. The maintenance dose of cocaine was reinstated after each substitution test for a period of at least 4 days and until the number of reinforces per day maintained by cocaine and food returned to baseline levels.

Test compound evaluation. Test compounds are evaluated using a pre-treatment procedure test. A first experiment examine the effects of non-contingent treatment with saline or test compound on food- and cocaine-responding. Test compounds are administered i.m.(or i.p. and p.o.) prior the session. Test compounds will be administered up to doses that produce either a statistical significant shift in the ascending limb of cocaine self-administration dose-effect curve, or eliminate responding during the first food component. In a second experiment at least three doses of test compounds are evaluated as pretreatments to a unit dose of cocaine at the peak of the cocaine dose-effect curve. These initial studies are used to identify a dose of the test compound that is behaviourally active in the drug elf-administration procedure. Once a behaviourally active dose of the test drug has been identified, that dose is administered as a pre-treatment to a range of different cocaine unit doses. In this way, it can be determined the effect of a behaviourally active dose of the test drug on the entire cocaine dose-effect curve. Other doses of the test compounds can be also tested.

Data Analysis. The total numbers of injections or food pellets delivered per day were determined as response rate. Data for the effects of the test compound on self-administration of cocaine are evaluated using a one or two-factor ANOVA. A significant ANOVA was followed by individual means comparison using the Duncan post hoc test. The criterion for significance was set at $p \leq 0.05$.

The invention claimed is:

1. A method of treating Restless Leg Syndrome in a human in need thereof, comprising administering to said human a therapeutically effective amount of safinamide ((S)-(+)-2[4-(3-fluorobenzyloxy)-benzylamino]propanamide) or a pharmaceutically acceptable acid salt thereof.

2. The method of claim 1, further comprising administering a therapeutically effective amount of levodopa.

3. The method of claim 2, further comprising administering a therapeutically effective amount of a decarboxylase inhibitor.

4. The method of claim 3, wherein said decarboxylase inhibitor is selected from the group consisting of carbidopa and benserazide.

5. The method of claim 1, further comprising administering a therapeutically effective amount of a dopamine agonist.

6. The method of claim 5, wherein said dopamine agonist is chosen from the group consisting of bromocriptine, cabergoline, lisuride, pergolide, ropinirole, apomorphine, sumanirole, rotigotine, talipexole, dihydroergocriptine and pramipexole.

7. The method according to claim 1, wherein said therapeutically effective amount of safinamide is from about 0.3 to about 100 mg/kg body weight per day.

8. The method of claim 2, wherein the Restless Leg Syndrome is idiopathic.

9. The method of claim 8, further comprising administering a therapeutically effective amount of levodopa.

10. The method of claim 9, further comprising administering a therapeutically effective amount of a decarboxylase inhibitor.

11. The method of claim 10, wherein said decarboxylase inhibitor is chosen from the group consisting of carbidopa and benserazide.

12. The method of claim 8, further comprising administering a therapeutically effective amount of a dopamine agonist.

13. The method of claim 9, wherein said dopamine agonist is chosen from the group consisting of bromocriptine, cabergoline, lisuride, pergolide, ropinirole, apomorphine, sumanirole, rotigotine, talipexole, dihydroergocriptine and pramipexole.

14. The method according to claim 8, wherein said therapeutically effective amount of safinamide is from about 0.3 to about 100 mg/kg body weight per day.

* * * * *